US006763081B2

(12) United States Patent
Tam (10) Patent No.: US 6,763,081 B2
(45) Date of Patent: Jul. 13, 2004

(54) CONE BEAM COMPUTED TOMOGRAPHY IMAGING SYSTEM AND METHOD PROVIDING EFFICIENT UTILIZATION OF DETECTOR AREA

(75) Inventor: Kwok Tam, Edison, NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 11 days.

(21) Appl. No.: 10/262,761

(22) Filed: Oct. 2, 2002

(65) Prior Publication Data

US 2004/0066876 A1 Apr. 8, 2004

(51) Int. Cl.[7] .................................................. G21K 1/12
(52) U.S. Cl. ........................... 378/4; 378/901; 378/146
(58) Field of Search .......................... 378/4, 901, 146, 378/15

(56) References Cited

U.S. PATENT DOCUMENTS

| 5,257,183 A | | 10/1993 | Tam | |
|---|---|---|---|---|
| 5,383,119 A | | 1/1995 | Tam | |
| 5,463,721 A | * | 10/1995 | Tam | ............................ 345/427 |
| 5,706,325 A | * | 1/1998 | Hu | ................................ 378/4 |
| 6,014,419 A | * | 1/2000 | Hu | ................................ 378/4 |

OTHER PUBLICATIONS

Feldkamp et al., "Practical Cone–Beam Algorithm", Journal of the Optical Society of America, vol. 1, pp. 612–619, 1984.
Kudo et al., "An Extended Completeness Condition for Exact Cone–Beam Reconstruction and Its Application", IEEE Nucl. Sci Symp. Conf. Record. 1994, Norfolk, VA pp 1710–1714.

* cited by examiner

Primary Examiner—Craig E. Church
Assistant Examiner—Irakli Kiknadze
(74) Attorney, Agent, or Firm—Donald B. Paschburg; F. Chau & Associates, LLP (57) ABSTRACT

Improved image reconstruction methods for cone beam ROI (region of interest) imaging of long objects with an area detector using a two or more circular scans and a connecting line scan, wherein essentially the entire detector area is utilized for acquiring cone beam data for all source positions.

12 Claims, 8 Drawing Sheets

$$v = -H\left(1 + \frac{u^2}{R^2}\right)$$

Top Circle
FIG. 9(a)

Middle Circle
FIG. 9(b)

Bottom Circle
FIG. 9(c)

CONE BEAM COMPUTED TOMOGRAPHY IMAGING SYSTEM AND METHOD PROVIDING EFFICIENT UTILIZATION OF DETECTOR AREA

TECHNICAL FIELD OF THE INVENTION

The present invention relates generally to 3-dimensional (3D) computerized tomography (CT) and, more specifically, to an improved cone beam CT system and method for efficiently acquiring projection data for image reconstruction of a region of interest using circular scans, wherein the detector area is optimally utilized for all source positions.

BACKGROUND

A system employing cone beam geometry has been developed for three-dimensional (3D) computed tomography (CT) imaging that comprises a cone beam x-ray source and a 2D area detector. An object to be imaged is scanned, preferably over a 360 degree angular range and along its entire length, by any one of various methods wherein the position of the area detector is fixed relative to the source, and relative rotational and translational movement between the source and object provides the scanning (irradiation of the object by radiation energy). The cone beam approach for 3D CT has the potential to achieve 3D imaging in both medical and industrial applications with improved speed, as well as improved dose utilization when compared with conventional 3D CT apparatus (i.e., a stack of slices approach obtained using parallel or fan beam x-rays).

As a result of the relative movement of the cone beam source to a plurality of source positions (i.e., "views") along the scan path, the detector acquires a corresponding plurality of sequential sets of cone beam projection data (also referred to herein as cone beam data or projection data), each set of cone beam data being representative of x-ray attenuation caused by the object at a respective one of the source positions. The cone beam projection data is then processed to reconstruct a 3D image of the object using image reconstruction methods known in the art.

Various methods have been developed for 3D image reconstruction for cone beam x-ray imaging systems. For example, a back projection cone beam image reconstruction technique is described in U.S. Pat. No. 5,257,183, which issued on Oct. 26, 1993 to Kwok C. Tam, entitled "*Method and Apparatus for Converting Cone Beam X-Ray Projection Data To Planar Integral and Reconstructing a Three-Dimensional Computerized Tomography (CT) Image of an Object*", which is incorporated herein by reference. This patent discloses a method and apparatus for converting cone beam data to values representing planar integrals on any arbitrary set of planes in Radon space for 3D image reconstruction through an inverse Radon transformation. Back projections can be mathematically accomplished for a cone beam source by inverse Radon transforming suitable planar integrals. The planar integrals are computed from detector integrals which utilize the measured cone beam projection data, i.e., the detected attenuated intensity representative of the density distributions of the object. The use of a cone beam source expedites data acquisition. A direct Radon inversion of three dimensional cone beam data from a cone beam source is not possible. Thus, before an inverse Radon transform can be undertaken in a three dimensional cone beam data implementation, the cone beam detector integrals must be reconfigured into planar integrals suitable for inverse Radon transformation. U.S. Pat. No. 5,257,183 discloses a method for image reconstruction by calculating Radon derivative data from the acquired cone beam data. The Radon derivative data is typically determined by calculating line integrals for a plurality of line segments drawn in the acquired cone beam data. Radon space driven conversion of the derivative data is used to develop an exact image reconstruction of a region-of-interest (ROI) in the object.

Figure 1:
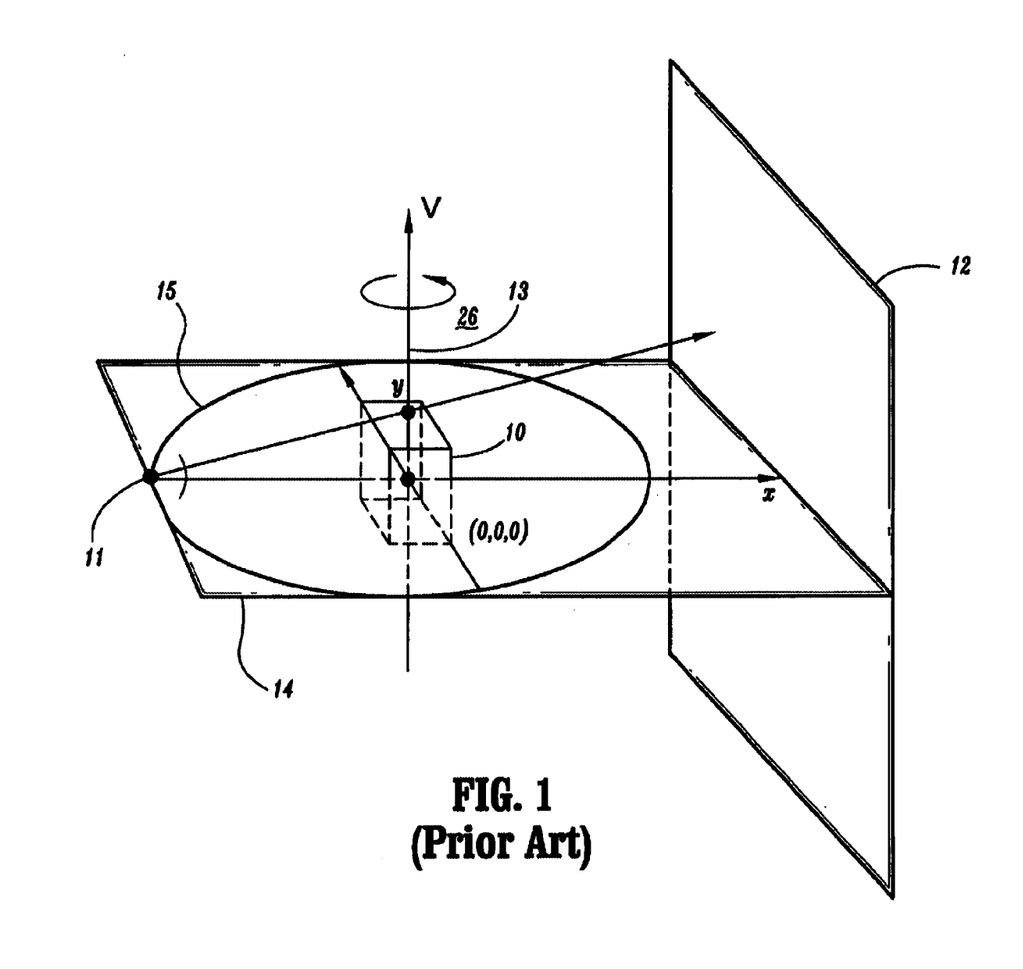
FIG. 1 illustrates a conventional scanning geometry for three dimensional CT scanning.

FIG. 1 illustrates a typical circular scanning geometry for three dimensional CT scanning employing cone beam geometry. An object 10 to be imaged is positioned within a field of view between a cone beam point source 11 and a two dimensional detector array 12 that acquires cone beam projection data. An axis of rotation 13 passes through the field of view and the object 10. A midplane 14 is defined as the plane that (i) is normal to the axis of rotation 13 and (ii) contains the cone beam point source 11. In the exemplary embodiments described herein, the axis of rotation 26 is the v axis, having its origin (0,0,0) at its intersection with the midplane. The coordinate system is fixed relative to the source 11 and detector 12. When scanning the object 10 at a plurality of angular positions, the source 11 moves relative to the object 10 and the field of view rotates along a circular scanning trajectory 15 lying in the midplane 14, while the detector 12 remains fixed with respect to the source 11 (or alternatively the object 10 can be rotated while the source 11 and detector 12 remain stationary). Data is acquired at a plurality of source positions during the scan. Data collected at the detector 12 represent line integrals through the object 10. The approach to reconstruction then embodies calculating planar integrals on a set of planes from various line integrals through the object, then performing an inverse Radon transform on the planar integrals to reconstruct a three dimensional image of the object. It is known that data collected in such a single circular scan is incomplete and artifacts may be introduced into the reconstructed image.

One image reconstruction method that uses two circular scans and a Radon transform approach to three dimensional CT imaging is disclosed, for example, in U.S. Pat. No. 5,383,119, which issued on Jan. 17, 1995 to Kwok Tam, entitled "*Method and Apparatus For Acquiring Complete Radon Data for Exactly Reconstructing a Three Dimensional Computerized Tomography Image Of a Portion of an Object Irradiated By a Cone Beam Source*", which is incorporated herein by reference. This patent discloses a method for imaging a region of interest (ROI) in a long object by scanning the ROI in 2 circular scan paths and a line scan that connects the two circular scans. The method enables exact 3D reconstruction of the image of a portion of interest of an object in the field of view of a cone beam source by selectively disregarding unwanted Radon data which may corrupt the imaging process and selectively recovering Radon data that would otherwise be lost. The method enables acquisition of a complete Radon data set through proper choice of scanning configuration and selective partitioning and manipulation of the acquired data.

Figure 2:
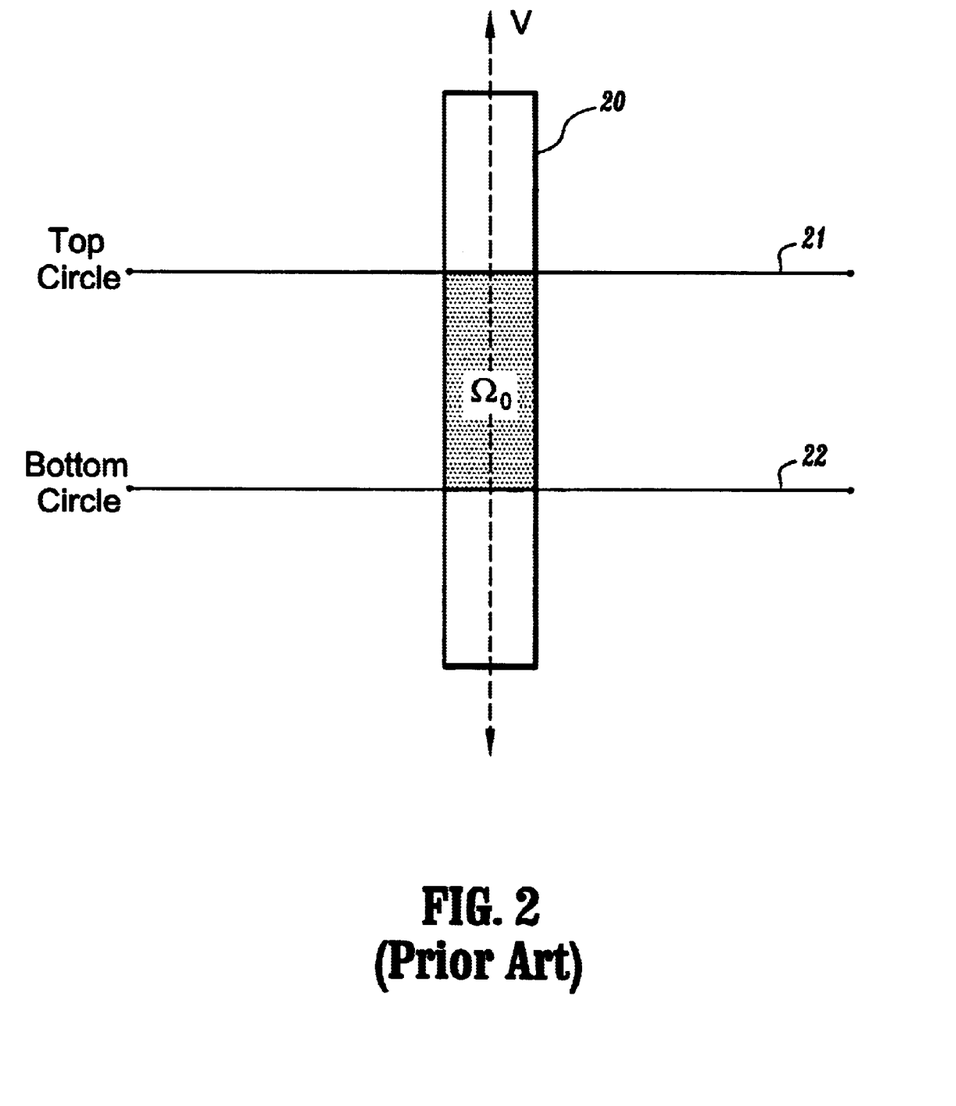
FIG. 2 illustrates a ROI (region of interest) that is reconstructed within a long object using a conventional data combination method for two circular scans.
Figure 3:
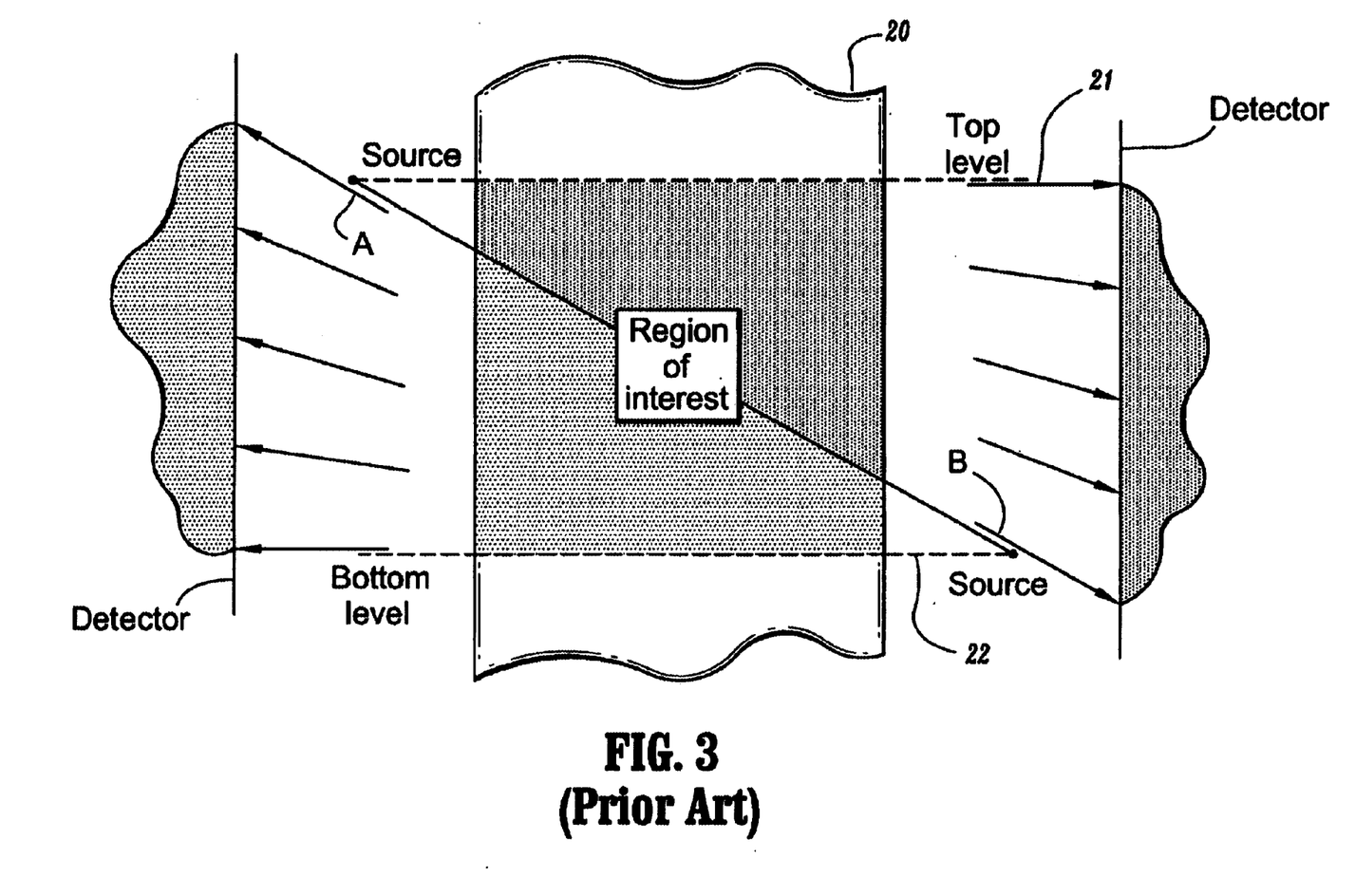
FIG. 3 illustrates the conventional data combination method for combining cone beam data from 2 circular scan paths for reconstructing the ROI in FIG. 2.

More specifically, referring to FIG. 2, a ROI $\Omega_o$ within a long object 20 (e.g., human body) is reconstructed by cone beam data collected by (i) an upper scan trajectory 21 and lower scan trajectory 22, which are taken to be spaced circular trajectories that are normal to the axis of rotation v, and (ii) a connecting line scan. A circular scan is performed for both the upper and lower bounds of the ROI and the data from the two circular scans are combined in such a manner as to appropriately reconstruct the ROI. FIG. 3 depicts the method for combining the cone beam data from two circular scan paths for reconstructing the ROI in a long object, wherein cone beam source positions A and B correspond to the top and bottom scans, respectively. In general, processing the cone beam data for an exact image reconstruction involves filtering, either implicitly or explicitly, all line segments on the detector (i.e., the integration line segments). In the data combination process, at each cone beam view, the line segments being filtered are restricted to only the cone beam data bound by the angular ranges as depicted in FIG. 3. In this manner, the totality of the cone beam data from all the contributing source positions covers every plane of integration intersecting the ROI in its entirety without any overlap.

More specifically, an image reconstruction method described in the above-incorporated U.S. Pat. No. 5,383,119 comprises the steps of performing a circular scan using a cone beam source along a circular path enclosing a ROI at the upper and lower extent of the ROI and joining the upper and lower circular scan paths by a connecting scan path. The upper, lower, and connecting scan paths collectively define a complete scan path for the ROI. Then, each plane of integration corresponding to a data point in Radon space is selectively partitioned based on the intersection of the plane with the ROI. Then, based on the partitioning, the cone beam data is selectively manipulated to discard data that is not directly attributable to the ROI and to recover otherwise missing data directly attributable to the ROI.

The process of selectively portioning each plane of integration comprises categorizing each plane of integration based on the manner in which the plane intersects the ROI. More specifically, to assess the adequacy of the filling of Radon space with Radon data, each integration plane that contributes to points in Radon space is categorized as follows: (i) a plane that does not intersect the ROI; (ii) a plane that intersects the ROI only; (iii) a plane that intersects the ROI and also either the region above the ROI or the region below the ROI, but not both; and (iv) a plane that intersects the ROI and also both the region above and the region below the ROI.

The process of selective manipulation generally comprises selectively disregarding cone beam data contributed from regions beyond the ROI in the long object to eliminate otherwise image corrupting data and selectively combining cone beam data obtained from the upper and lower scans to recover data otherwise missing due to corruption by regions beyond the ROI. In particular, for case (i), the planar integral will be zero so the corresponding cone beam data is discarded. For case (ii), the planar integral is computed from the cone beam data based on the methods described in the above-incorporated U.S. Pat. No. 5,257,183. For case (iii), the planar integral is computed from the top scan data or the corresponding bottom scan data as follows: the unwanted contribution of that portion of the object beyond the ends of the ROI to the computation of the planar integrals is eliminated by discarding all the cone beam data whose paths traverse the region beyond the ends of the ROI. For case (iv), the data is selectively manipulated by selectively combining cone beam data from top and bottom level scans for each plane intersecting both the top and bottom levels of the ROI, as diagrammatically shown in FIG. 3. Finally, missing Radon data is then filled in by any scan connecting the upper and lower circular scans. Further details of the above method for acquiring complete Radon data for exact image reconstruction of a 3D image of the ROI can be found in the above-incorporated U.S. Pat. No. 5,383,119.

One known method for restricting the cone beam data to the appropriate angular range is accomplished by a "masking" process, which facilitates efficient 3D CT imaging when only the ROI in the object is to be imaged, as is normally the case. During a scan, the scanning trajectory is sampled at a plurality of source positions where cone beam energy is emitted toward the ROI. After passing through the ROI the residual energy at each of the source positions is acquired on the area detector as a given one of a plurality of sets of cone beam data. Each set of the cone beam data is then "masked" so as to remove a portion of the cone beam data that is outside a given sub-section of a projection of the ROI in the object and to retain cone beam projection data that is within the given sub-section. The shape of each mask for a given set of cone beam data will vary based on the scan orbit. The cone beam data that is retained (via the masking process) is then processed so as to develop reconstruction data. An exact image of the ROI is developed by combining the reconstruction data from the various source positions which intersect a common integration plane. As such, the masks are commonly referred to as "data-combination" masks.

Typically, and in a preferred embodiment of the present invention, projection data for image reconstruction is acquired by applying a "mask" to each set of the projection data so that data inside the boundaries of each mask form a corresponding plurality of masked 2D data sets.

Figure 4A:
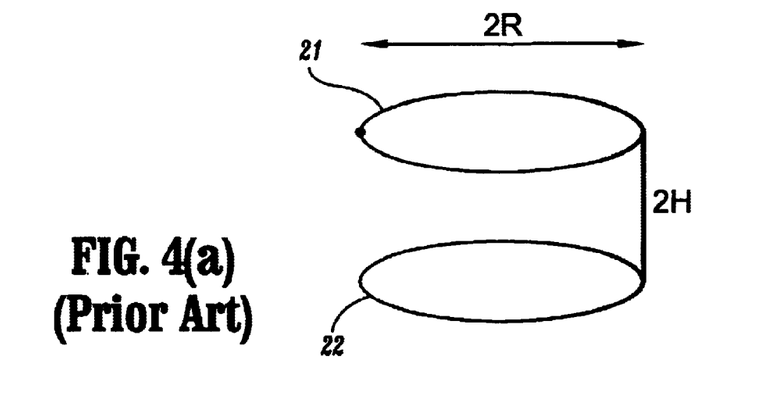
FIG. 4a illustrates parameters of the circular orbits that are used for determining the masks depicted in FIGS. 4b and 4c for the upper and lower circular scans, respectively.
Figure 4B:
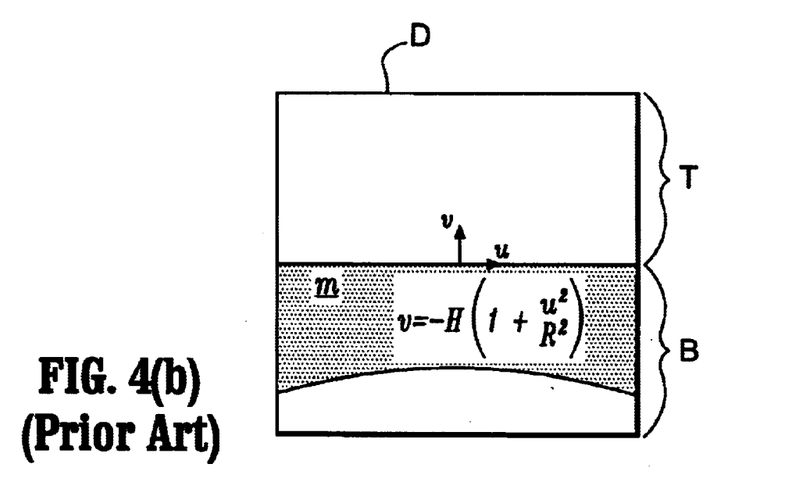

FIG. 4 is a diagram that illustrates masks used in the exemplary embodiments of FIGS. 2 and 3, wherein circular scans are taken along the upper and lower boundaries of the ROI. FIG. 4a illustrates the upper circular scan trajectory 21 and lower circular scan trajectory 22 which are separated by a distance of 2H (line scan) and each trajectory having a diameter of 2R. FIG. 4b illustrates a mask M which is applied to the cone beam data on detector D for the upper circular scan 21. As shown, the mask M boundaries comprise a top curve and a bottom curve, which are formed by projecting the upper circular scan path from a current source position. More specifically, for a flat detector D located at the rotation axis such that the line connecting the source to the detector origin is normal to the detector plane, the equation of the mask M for a given source position on the top circular scan path is defined by the following:

Top Boundary: v=0

Figure 4C:
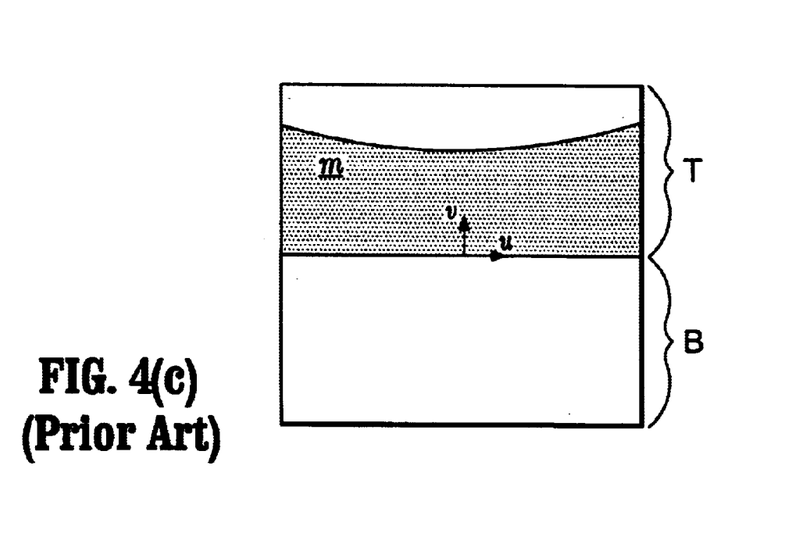

Bottom Boundary $$v = -H\left(1 + \frac{u^2}{R^2}\right)$$

where u and v are the Cartesian coordinate axes of the detector with the v axis coinciding with the rotation axis and R is the radius of the circles. FIG. 4c illustrates a mask M for the bottom circular scan 22, which is just the inverse of the mask for the upper scan.

As discussed above, in medical x-ray scanners, the source and the area detector are always fixed relative to each other, with the source projecting onto the center of the detector. In such a framework, when the data masks illustrated in FIG. 4 are used to filter the cone beam data, only one half of the detector area is essentially utilized in capturing data at each of the circular scans, while the other half of the detector is not utilized at all. For instance, as shown in FIG. 4b, the cone beam data in the upper half of the detector, i.e., v>0, is filtered out via the mask and consequently, that portion of the detector is essentially not used for capturing data during the circular scan.

Accordingly, an improved image reconstruction method that would enable efficient utilization of the detector area, is highly desirable.

SUMMARY OF THE INVENTION

The present invention is directed to a method for cone beam region of interest imaging of long objects with an area detector employing a series of circular scans, wherein the detector area is essentially fully utilized for all source positions.

In one aspect of the invention, a method for imaging a region of interest (ROI) of an object uses cone beam computed tomography, wherein a cone beam source is fixed with respect to a two dimensional detector. The method comprises performing a first and second circular scan along a first and second extent, respectively, of a ROI within an object being imaged. The cone beam source and detector are fixed such that during the first and second circular scans, one half of the detector area is used to acquire cone beam projection data corresponding to the ROI and a second half of the detector area is used to acquire cone beam projection data corresponding to a first and a second extended portion of the object, which extend beyond the first and second extents, respectively, of the ROT. A line scan is taken along the object connecting the first and second circular scans. The ROI is reconstructed by selectively combining the cone beam projection data corresponding to the ROI acquired from the first and second circular scans, and the first and second extended portions of the object are reconstructed using the cone beam projection data corresponding to the extended portions acquired from the first and second circular scans and the cone beam projection data acquired from the line scan. An extended ROI is reconstructed by combining the reconstructed ROI and reconstructed first and second extended portions These and other objects, features and advantages of the present invention will be described or become apparent from the following detailed description of preferred embodiments, which is to be read in connection with the accompanying drawings.

BRIEF DESCRIPTION OF DRAWINGS

FIG. 4 generally illustrates a method for masking cone beam data for the two circular scan paths on a flat detector for the data combination method shown in FIG. 3, wherein

FIG. 5 generally illustrates a cone beam data acquisition process for an image reconstruction method according to an embodiment of the present invention, wherein

FIG. 6 generally illustrates a cone beam data acquisition process for an image reconstruction method according to an embodiment of the present invention, wherein

DETAILED DESCRIPTION OF PREFERRED EMBODIMENTS

The present invention is directed to improved image reconstruction methods for cone beam ROI imaging of long objects with an area detector using a series of circular scans, wherein essentially the entire detector area is utilized for all source positions. More specifically, preferred embodiments of the invention comprise extensions of the data acquisition and image reconstruction techniques disclosed in the above-incorporated U.S. Pat. No. 5,383,119 to improve utilization of the detector. Rather than filter out (via a mask) the portion of the cone beam projection data (which is captured by the circular scans on the ROI boundaries) that lies outside the ROI, the cone beam data outside the ROI is preferably processed using the methods disclosed in the reference by Kudo, et al., entitled "*An Extended Completeness Condition for Exact Cone-Beam Reconstruction and its Application*", IEEE Nucl. Sci Symp. Conf. Record, 1994, Norfolk, Va., pp 1710–1714 (referred to herein as "Kudo"), which is incorporated herein by reference. Further, the cone beam data within the ROI is acquired and processed using the methods disclosed in the above-incorporated U.S. Pat. No. 5,383,119.

Image reconstruction methods according to the invention provide reconstruction of an extended ROI, i.e., a ROI that includes a portion of the object that lies beyond the boundary extents of the circular scans. Advantageously, image reconstruction methods according to the invention enable virtually full utilization of the detector, while providing reconstruction of a longer (extended) ROI with the same projection data acquired by the scanning trajectories for the method of U.S. Pat. No. 5,383,119, within the same scan time. In other words, by optimally utilizing the detector, a longer volume can be reconstructed for the same data acquisition scan time.

Figure 5A:
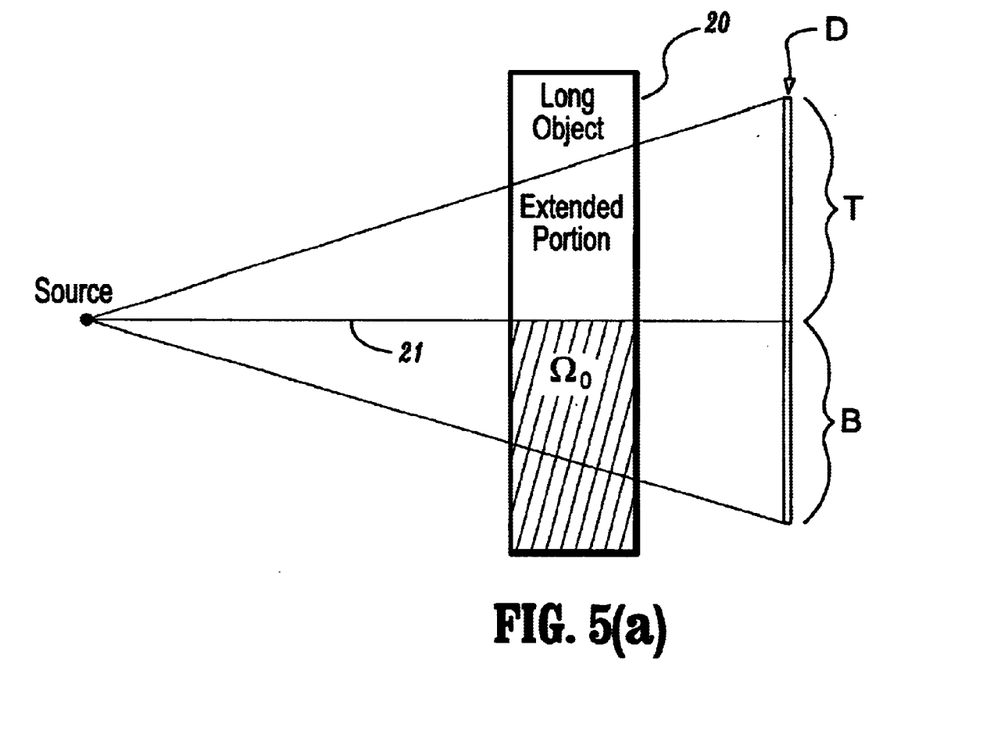
FIG. 5a illustrates reconstruction of an extended portion from a ROI at a single source position on an upper circular scan path and FIG. 5b illustrates detector utilization of the upper circular scan.
Figure 5B:
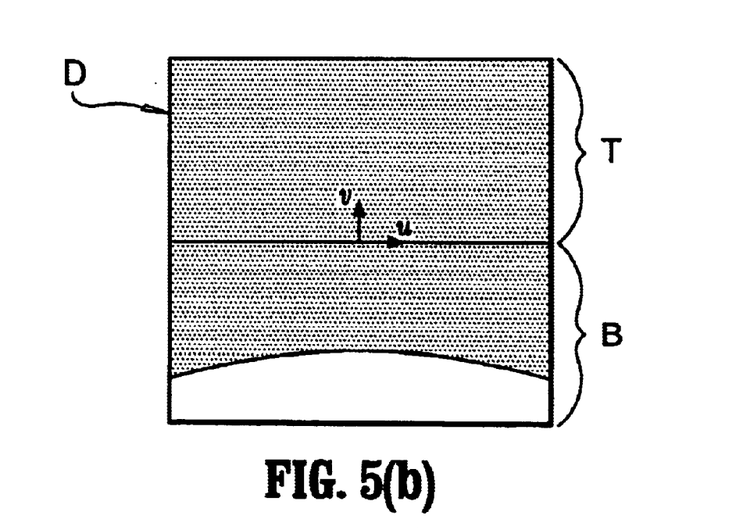

Details of image reconstruction methods according to the invention will now be discussed with reference to FIGS. 5–9. FIG. 5 generally illustrates a cone beam data acquisition process for an image reconstruction method according to an embodiment of the present invention. More specifically, FIG. 5($a$) illustrates a given source position on the upper circular scan 21, wherein an "extended" portion of the long object 20 (which is located above the desired ROI $\Omega_o$ in the figure) is reconstructed using cone beam projection data captured on the top half (T) of the detector D. FIG. 5($b$) illustrates the utilization of the detector D for the upper circular scan depicted in FIG. 5($a$). As shown, the cone beam projection data on the upper half (T) of the detector D is not masked (filtered) out but rather fully utilized. The cone beam projection data that is captured on the detector portion T (i.e., v>0) is processed using the methods described in the Kudo reference, whereas the cone beam projection data that is captured on the detector portion (B) (i.e., for v≤0)is processed for data combination with the bottom circular scan path data using the methods disclosed in the above-incorporated U.S. Pat. No. 5,383,119. This is to be contrasted with the method depicted in FIGS. 3 and 4b, for example, wherein the cone beam projection data for v>0 is filtered out via mask M such that the cone beam projection data on the top half (T) of detector D is not utilized for image reconstruction.

Figure 6A:
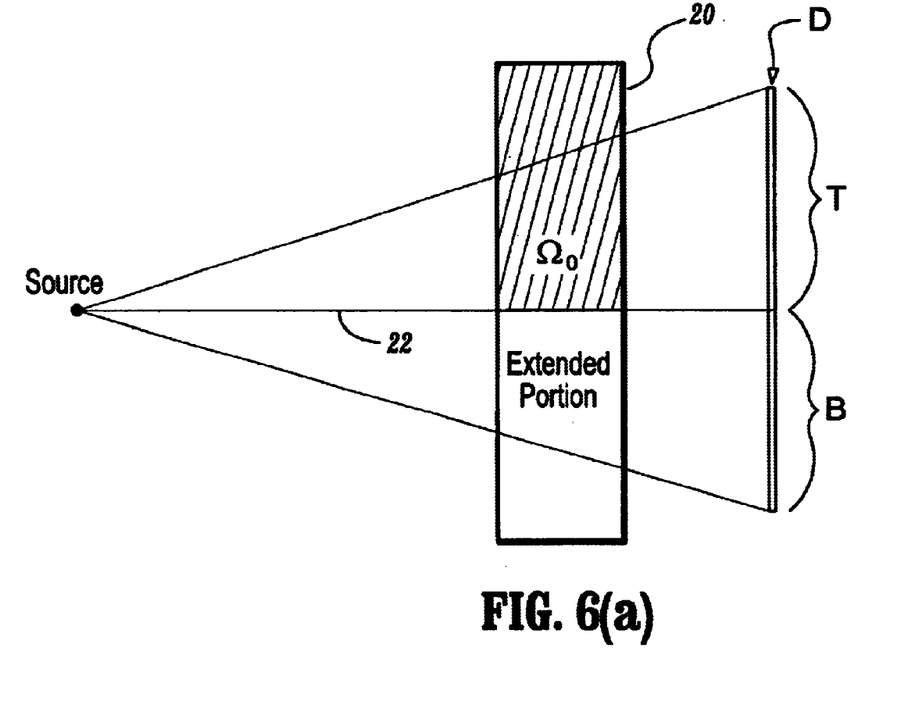
FIG. 6a illustrates reconstruction of an extended portion from a ROI at a single source position on a lower circular scan path and FIG. 6b illustrates detector utilization of the lower circular scan.
Figure 6B:
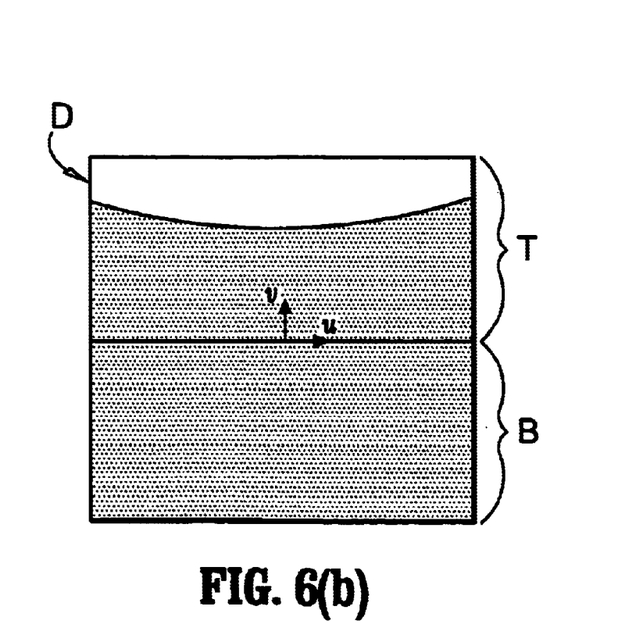

A similar cone beam data acquisition process is applied for the lower circular scan 22 as depicted in FIG. 6. In particular, FIG. 6(a) illustrates a given source position on the lower circular scan 22, wherein an "extended" portion of the long object 20 (which is located below the desired ROI $\Omega_o$ in the figure) is reconstructed using cone beam projection data captured on the bottom half (B) of the detector D. FIG. 6(b) illustrates the utilization of the detector D for the lower circular scan 22 depicted in FIG. 6(a). As shown, the cone beam projection data on the lower half (B) of the detector D is not masked (filtered) out, but rather fully utilized. The cone beam projection data that is captured on the bottom half (B) of the detector (i.e., v<0) is processed using the methods described in the Kudo reference, whereas the cone beam projection data that is captured on the upper half (T) of the detector D (i.e., for v≧0) is processed for data combination with the upper circular scan path data using the methods disclosed in the above-incorporated U.S. Pat. No. 5,383,119. This is to be contrasted with the method depicted in FIGS. 3 and 4c, for example, wherein the cone beam projection data for v<0 is filtered out via mask M such that the cone beam projection data on the bottom half (B) of detector D is not utilized for image reconstruction.

Figure 7:
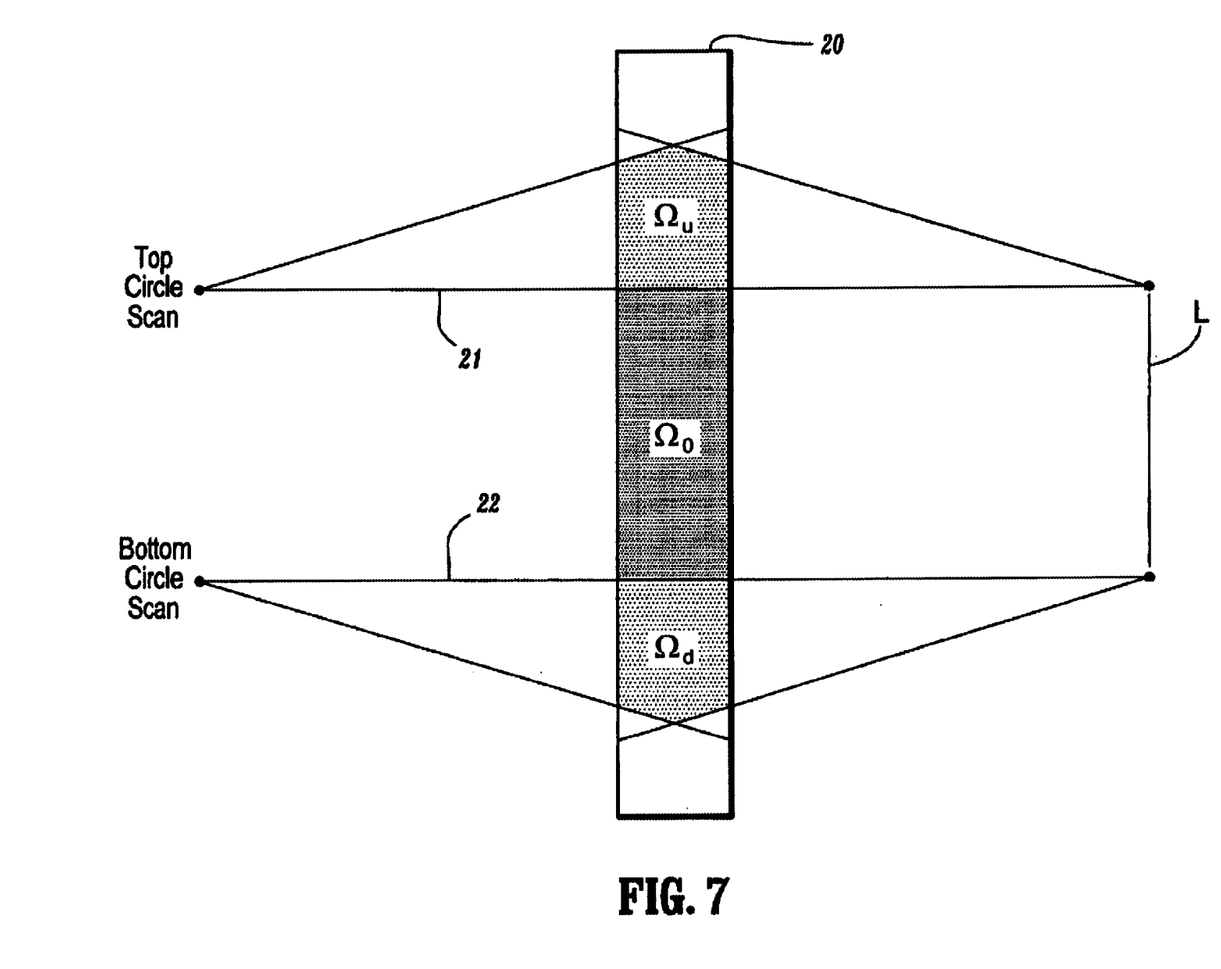
FIG. 7 illustrates an extended ROI that is reconstructed using cone beam data that is acquired from the two circular scan paths in FIGS. 5 and 6 using an image reconstruction method according to an embodiment of the invention.

FIG. 7 illustrates an extended ROI, comprising a ROI $\Omega_o$, and extended portions $\Omega_u$ and $\Omega_d$, which is reconstructed using cone beam data that is acquired from two circular scan paths 21 and 22 (FIGS. 5 and 6), and a connecting line scan L, using an image reconstruction method according to an embodiment of the invention. When the entire top circular scan data is processed using the method depicted in FIG. 5, the portion of the cone beam image with v>0 yields reconstruction of the volume $\Omega_u$ shown in FIG. 7. Similarly, when the entire bottom circular scan data is processed using the method depicted in FIG. 6, the portion of the cone beam image with v<0 yields reconstruction of the volume $\Omega_d$ shown in FIG. 7. The total reconstructed volume with the two circular scan paths is extended from $\Omega_o$ to $\Omega_u \cup \Omega_o \cup \Omega_d$.

Further details of the data acquisition and processing method for reconstructing the extended ROI depicted in FIG. 7, will now be explained in further detail. As discussed above, the method disclosed in the above-incorporated U.S. Pat. No. 5,383,119 is extended to perform a data acquisition and image reconstruction process that improves utilization of the detector and provides reconstruction of an extended ROI, i.e., a reconstructed ROI which is larger that the reconstructed ROI obtained using the method U.S. Pat. No. 5,383,119, but with the same scanning paths and scanning time as the conventional method. To improve the utilization of the detector, the cone beam data in the v>0 portion (see FIG. 5(b)), that is obtained from the upper circular scan, together with the cone beam data from a line scan, are used to reconstruct the portion $\Omega_u$ of the long object that extends from the end of $\Omega_o$ using the Kudo method. Similarly, using the Kudo method, the cone beam data in the v<0 portion (see FIG. 6(b)), that is obtained from the lower circular scan, together with the cone beam data from the line scan, are used to reconstruct the portion $\Omega_d$ of the long object that extends from the end of $\Omega_o$.

Details of a preferred method for processing cone beam data for the extended portions, $\Omega_u$ and $\Omega_d$, using the Kudo method will now be provided. First, the portion of the cone beam image data that corresponds to the extended portions, i.e., the cone beam data for v>0 for the upper circular scan, and the cone beam data for v<0 for the lower circular scan, is processed using the well-known "Feldkamp" algorithm, which is disclosed for example in the article by Feldkamp, et al., entitled "*Practical Cone-Beam Algorithm*", Journal of the Optical Society of America, Vol. 1, pp. 612–619, 1984, which is incorporated herein by reference. Essentially, with the Feldkamp method, a ramp filtering process is applied to the relevant projection data of the circular scans.

Next, the line scan data are processed to fill in the data missing in the circle scan data, i.e. those integration planes which do not intersect the circle scan. Essentially, with this process, space-variant filtering is applied to the linear orbit (line scan), where a redundancy function is employed to extract the 3-D Radon Data that is inaccessible from the circular orbits and discard other multiply measures 3-D Radon data. More specifically, the line scan data are processed as follows:

For each angle θ: (1) compute all line integrals at angle θ; (2) compute the derivative of the line integrals; and (3) compute a 2D backprojection of the line integral derivatives. Steps (1), (2) and (3) are performed on each line such that the integration plane defined by the line and the source position does not intersect the circle scan. The last step (4) is to compute the derivative of the resultant 2D backprojection image in the horizontal direction. The above process results in reconstruction of the extended regions $\Omega_u$ and $\Omega_d$ as shown in FIG. 7. Further, as noted above, the method disclosed in the above-incorporated U.S. Pat. No. 5,383,119, is used to reconstruct the region $\Omega_o$. The combination of the different reconstructed regions yield the extended ROT shown in FIG. 7.

Advantageously, since the data acquisition process according to one embodiment of the invention utilizes the same scan paths as disclosed in U.S. Pat. No. 5,383,119 (i.e., two circular scans and one connecting line scan), one can obtain reconstruction of an extended ROT, while maintaining the same scan time and fully utilizing the detector area.

Figures 8, 9A, 9B, 9C:
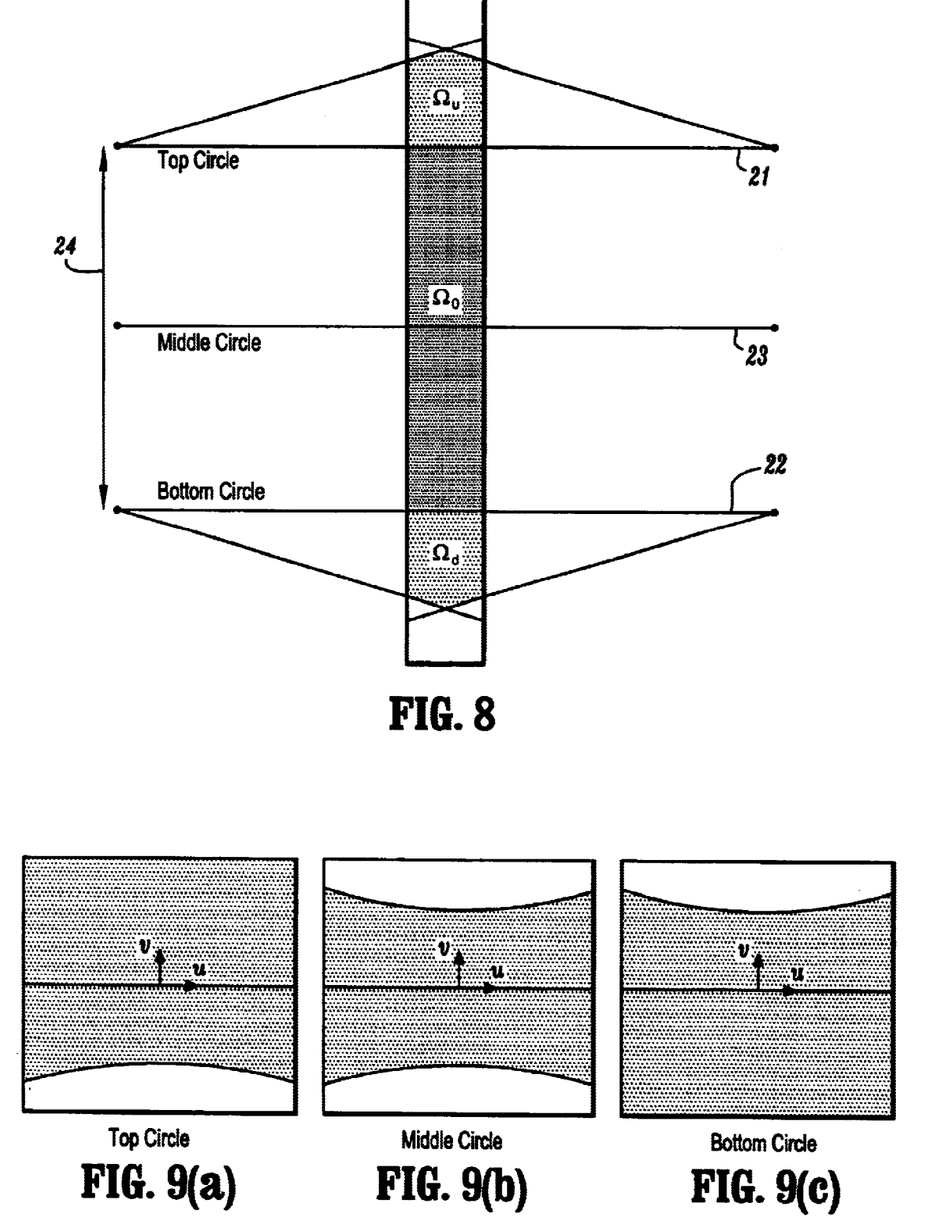
FIG. 8 illustrates an extended ROI that is reconstructed from three circular scan paths using an image reconstruction method according to another embodiment of the invention.
FIGS. 9a, 9b and 9c illustrate detector utilization of upper, middle and lower circular scans, respectively, for an image reconstruction method according to an embodiment of the invention that reconstructs the extended ROI depicted in FIG. 8.

In other embodiments of the invention, the data acquisition and image reconstruction may be performed using more than two circle scans. For example, FIG. 8 illustrates an extended ROT that is reconstructed from three circular scan paths, an upper scan 21, lower scan 22 and middle scan 23, and one connecting line scan 24. The volume $\Omega_o$ between the upper and lower scans 21, 22 is reconstructed with the data combination method disclosed in the incorporated U.S. Pat. No. 5,383, 119. Further, the portion of the cone beam image with v>0 for source positions on the upper circular scan path 21, as well as the portion of the cone beam image with v<0 for source positions on the lower circular scan 22, is processed using the Kudo method as discussed above. FIGS. 9a, 9b and 9c illustrate detector utilization of upper, middle and lower circular scans, respectively, for data acquisition and image reconstruction of the extended ROT shown in FIG. 8. Based on the teachings herein, an extension of the current method for 4 or more circular scans is readily apparent to one of ordinary skill in the art.

Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention. All such changes and modifications are intended to be included within the scope of the invention as defined by the appended claims.

What is claimed is:

1. A method for imaging a region of interest (ROI) of an object using cone beam computed tomography, wherein a cone beam source is fixed with respect to a two dimensional detector, the method comprising the steps of:

performing at least a first and a second circular scan along a first and a second extent, respectively, of a ROI within an object, wherein the cone beam source and detector are fixed such that during the first and second circular scans, one half of the detector area is used to acquire cone beam projection data corresponding to the ROI and a second half of the detector area is used to acquire cone beam projection data corresponding to a first and a second extended portion of the object, which extend beyond the first and second extents, respectively, of the ROI;

performing a line scan along the object connecting the first and second circular scans;

reconstructing the ROI by selectively combining the cone beam projection data corresponding to the ROI acquired from the first and second circular scans; and reconstructing the first and second extended portions of the object using cone beam projection corresponding to the extended portions acquired from the first and second circular scans and cone beam data acquired from the line scan.

2. The method of claim 1, further comprising the step of combining the reconstructed ROI and first and second extended portions to obtain a reconstructed image of an extended ROI.

3. The method of claim 1, wherein the step of reconstructing the first and second extended portions comprises the steps of ramp filtering the corresponding cone beam projection data of the first and second circular scans and space variant filtering the projection data corresponding to the line scan.

4. The method of claim 1, wherein the step of reconstructing the ROI comprises augmenting missing Radon data from the first and second circular scans using the projection data acquired from the line scan.

5. A program storage device readable by a machine, tangibly embodying a program of instructions executable by the machine to perform method steps for imaging a region of interest (ROI) of an object using cone beam computed tomography, wherein a cone beam source is fixed with respect to a two dimensional detector, the method steps comprising:

acquiring cone beam projection data from at least a first and second circular scan along a first and second extent, respectively, of a ROI within an object, wherein the cone beam source and detector are fixed such that during the first and second circular scans, one half of the detector area is used to acquire cone beam projection data corresponding to the ROI and a second half of the detector is used to acquire cone beam projection data corresponding to a first and a second extended portion of the object, which extend beyond the first and second extent, respectively, of the ROI;

acquiring cone beam projection data from a line scan along the object connecting the first and second circular scans;

reconstructing the ROI by selectively combining the cone beam projection data corresponding to the ROI acquired from the first and second circular scans; and reconstructing the first and second extended portions of the object using cone beam projection corresponding to the extended portions acquired from the first and second circular scans and cone beam data acquired from the line scan.

6. The program storage device of claim 5, further comprising instructions for combining the reconstructed ROI and first and second extended portions to obtain a reconstructed image of an extended ROI.

7. The program storage device of claim 5, wherein the instructions for reconstructing the first and second extended portions comprise instructions for ramp filtering the corresponding cone beam projection data of the first and second circular scans and space variant filtering the projection data corresponding to the line scan.

8. The program storage device of claim 5, wherein the instructions for reconstructing the ROI comprise instructions for augmenting missing Radon data from the first and second circular scans using the projection data acquired from the line scan.

9. A method for imaging a region of interest (ROI) of an object using cone beam computed tomography, comprising the steps of:

positioning an object to be imaged within a field of view between a cone beam point source and a two dimensional detector array, the cone beam point source and two dimensional detector being spatially fixed in relation to each other, wherein an axis of rotation v passes through the field of view and the object, wherein the cone beam point source is contained in a midplane that (i) is normal to the axis of rotation; (ii) is normal to a surface of the detector; and that (iii) intersects a center line of the detector that equally divides the detector area;

performing a first circular scan at various source positions along a first extent of a ROI of the object to acquire a first set of cone beam projection data by the detector;

performing a second circular scan at various source positions along a second extent of the object to acquire a second set of cone beam projection data by the detector, wherein the first and second extent of the object correspond to outer boundaries of a ROI along the rotation axis;

wherein the cone beam source and detector are fixed such that during the first and second circular scan, one half of the detector area is used to acquire cone beam projection data corresponding to the ROI and a second half of the detector area is used to acquire cone beam projection data corresponding to a first and a second extended portion of the object;

performing a line scan connecting the first and second circular scans to acquire a third set of cone beam projection data;

reconstructing an image of the ROI defined by the first and second extents by selectively combining a portion of the first set of acquired cone beam projection data corresponding to the ROI, a portion of the second set of acquired cone beam projection data corresponding to the ROI and the third set of cone beam projection data;

reconstructing an image of a first extended portion of the object that extends beyond the first extent of the ROI using the third set of cone beam projection data and a remaining portion of the first set of cone beam projection data that does not correspond to the ROI; and reconstructing an image of a second extended portion of the object that extends beyond the second extent of the ROI using the third set of cone beam projection data and a remaining portion of the second set of cone beam projection data that does not correspond to the ROI.

10. The method of claim 9, further comprising the step of combining the reconstructed images of the ROI and first and second extended portions to obtain an image of an extended ROI.

11. The method of claim 9, wherein the steps of reconstructing the first and second extended portions comprise the steps of ramp filtering the corresponding cone beam projection data of the first and second circular scans and space variant filtering the third set of cone beam projection data.

12. The method of claim 9, wherein the step of reconstructing the ROI comprises augmenting missing Radon data from the first and second circular scans using the third set of cone beam projection data.

* * * * *